United States Patent [19]

Yamasaki

[11] Patent Number: 5,064,951

[45] Date of Patent: Nov. 12, 1991

[54] NAPHTHALOCYANINE COMPOUND AND PRODUCTION THEREOF

[75] Inventor: Yasuhiro Yamasaki, Atlanta, Ga.

[73] Assignee: Orient Chemical Industries, Ltd., Osaka, Japan

[21] Appl. No.: 504,309

[22] Filed: Apr. 4, 1990

[30] Foreign Application Priority Data

Apr. 6, 1989 [JP] Japan .................................. 1-87230

[51] Int. Cl.$^5$ ...................... G03G 5/04; C07D 403/00

[52] U.S. Cl. ...................................... 540/128; 430/78

[58] Field of Search ........................... 540/128; 430/78

[56] References Cited

U.S. PATENT DOCUMENTS

| | | | |
|---|---|---|---|
| 2,613,129 | 10/1952 | McCorpmack et al. | 540/128 |
| 4,311,775 | 1/1982 | Regan | 430/78 |
| 4,492,750 | 1/1985 | Law et al. | 430/494 |

FOREIGN PATENT DOCUMENTS

| | | | |
|---|---|---|---|
| 252344 | 12/1985 | Japan . | |
| 16891 | 1/1986 | Japan | 540/128 |
| 25886 | 4/1986 | Japan | 540/120 |
| 163891 | 7/1986 | Japan | 540/128 |
| 215662 | 9/1986 | Japan | 540/128 |
| 122788 | 6/1987 | Japan | 540/128 |
| 233287 | 10/1987 | Japan | 540/128 |
| 39388 | 2/1988 | Japan | 540/128 |
| 72594 | 4/1988 | Japan | 540/128 |
| 72761 | 4/1988 | Japan | 540/128 |

OTHER PUBLICATIONS

Kumagai et al., Chemical Abstracts, vol. 106, 1977, Abstract 103817h.

Shibano et al., 1988, Chemical Abstracts, vol. 109, 1988, Abstract 1019939.

*Primary Examiner*—Mukund J. Shah

*Assistant Examiner*—E. C. Ward

*Attorney, Agent, or Firm*—Birch, Stewart, Kolasch & Birch

[57] ABSTRACT

Disclosed is a novel naphthalocyanine compound which strongly absorbs light or near infrared region and which is chemically stable and highly soluble to an organic solvent. The naphthalocyanine compound is represented by the following formula [1];

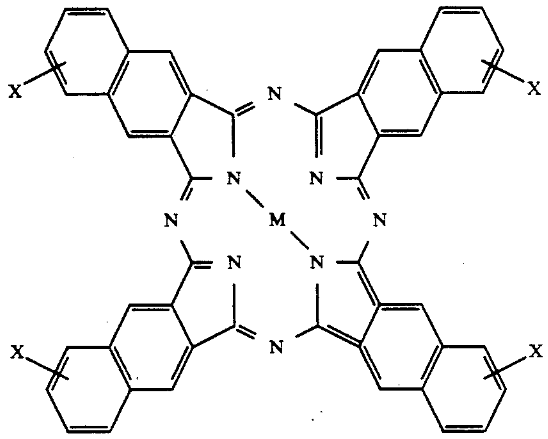

[1]

wherein X represents

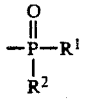

(provided that $R^1$ and $R^2$ respectively represent a hydroxyl group, an alkyl group, an aryl group or an alkoxy group.) and M represents 2H, a metal atom, a metal oxide residue or a metal chloride residue. The present invention also provides a process for producing the naphthalocyanine compound, an intermediate thereof and a process for producing the intermediate.

9 Claims, 18 Drawing Sheets

NAPHTHALOCYANINE COMPOUND AND PRODUCTION THEREOF

FIELD OF THE INVENTION

The present invention relates to a naphthalocyanine compound, an intermediate therefor and a process for producing them. More particularly, it relates to a novel naphthalocyanine compound which strongly absorbs light of near infrared region and which is chemically stable and highly soluble in an organic solvent.

BACKGROUND OF THE INVENTION

A naphthalocyanine compound which is known as a dyestuff absorbing near infrared light is stable to light and heat, and has excellent fastness.

The dyestuff which absorbs near infrared light is known to the art, for examples, cyanines, phthalocyanines, dithionickel complexes, naphthoquinones, anthraquinones, indophenols, azo compounds and the like. The dyestuff is applicable to optical disks, compact disks, laser printers, laser reading, electrophotographic photosensitive members, infrared cut filters for semiconductor light receptors and the like. It is also proposed in Japanese Kokai Publications (unexamined) 25886/1986, 163891/1986, 233287/1987, 72594/1988, 122788/1987, 39388/1988, 252344/1985 and 16891/1986 that the dyestuff is employed in the recording layer of the optical disk.

A dyestuff for a DRAW type optical recording medium is required to have a strong absorption in the region of a laser oscillation, a high reflectance, a high stability and forming abilities of a uniform recording medium layer.

However, the cyanine dyestuff is poor in color fastness to light, and therefore a recording medium using the cyanine dyestuff is insufficient in stability. The phthalocyanine or naphthalocyanine dyestuff is poor in solubility to a polar solvent, and therefore forms an uneven recording medium layer. In order to improve the solubility of the naphthalocyanine dyestuff, there are many patent applications, such as U.S. Pat. No. 4,492,750 and Japanese Kokai Publication (unexamined) 215662/1986 in which a naphthalene ring is substituted with an alkyl group, substituted silyl group, alkoxy group, phenoxy group or aralkoxy group; Japanese Kokai Publications (unexamined) 72761/1988 and 95269/1988 in which a center metal is substituted with an alkoxy group or alkylsiloxy group. The proposed naphthalocyanine dyestuffs damage guide digs on a substrate and are still insufficient in solubility to alcohols.

SUMMARY OF THE INVENTION

The present invention provides a novel naphthalocyanine compound which strongly absorbs light of near infrared region and which is chemically stable and highly soluble in an organic solvent. The naphthalocyanine compound is represented by the following formula [1];

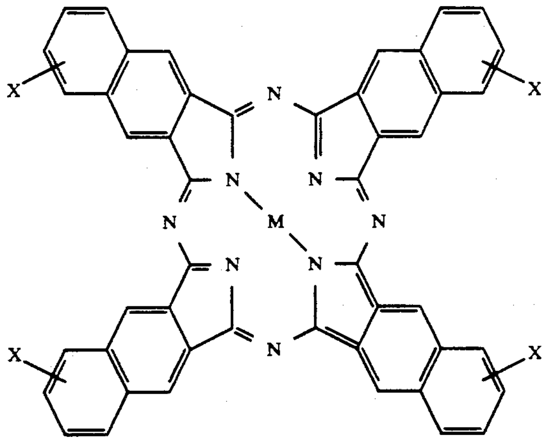

[1]

wherein X represents

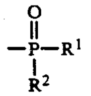

(provided that $R^1$ and $R^2$ respectively represent a hydroxyl group, an alkyl group, an aryl group or an alkoxy group) and M represents 2H, a metal atom, a metal oxide residue or a metal chloride residue.

The present invention also provides a process for producing the above mentioned naphthalocyanine compound.

Also, the present invention provides an intermediate suitable for producing the naphthalocyanine compound of the present invention.

Further, the present invention provides a process for producing the above mentioned intermediate.

DETAILED DESCRIPTION OF THE INVENTION

In the formula [1], examples of the substitutes X are $-P(=O)(C_6H_5)_2$, $-P(=O)(OC_2H_5)_2$, $-P(=O)(C_{10}H_{21})_2$ and $-P(=O)(OH)_2$. The substituent X may be substituted at any position of 5, 6, 7 and 8 potions of the naphthalene ring.

In the formula [1], the symbol M shows 2H, a metal atom, a metal oxide residue or a metal chloride residue. Examples of the metal atoms are Cu, Zn, Ni, Co, Fe, Ge, Sn, Pb, Ti, Cr, Mn, Al, In and the like. Examples of the metal oxide residues are

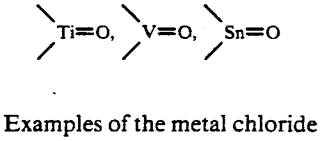

and the like. Examples of the metal chloride residues are

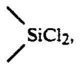

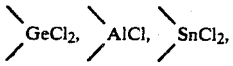

InCl and the like.

The 2,3-dicyanonaphthalene [2] having a substituent X which is represented by

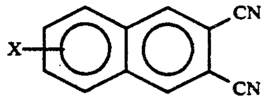

[2]

wherein X is the same as mentioned above, is an intermediate for producing the naphthalocyanine compound of the present invention. The substituent X may be substituted at either 5 or 6 position of the naphthalene ring.

The intermediate can be prepared by reacting 3- or 4-bromo-o-xylene with a phosphine oxide or a phosphite in the presence of a catalyst to form a X substituted-o-xylene [3] represented by

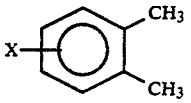

[3]

wherein X is the same as mentioned above, reacting it with N-bromosuccinimide to form a compound [4] represented by

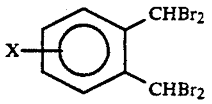

[4]

wherein X is the same as mentioned above, and then reacting the compound [4] with fumaronitrile [5] represented by

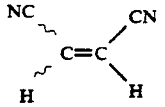

[5]

Examples of the phosphine oxides are chlorodiethyl phosphine oxide, chlorodiphenyl phosphine oxide and the like. Examples of the phosphites are methyl phosphite, ethyl phosphite, decyl phosphite and the like. The catalyst includes anhydrous nickel chloride or the like. The amount of the phosphine oxide is 1.0 to 1.1 mol based on 1 mol of 3- or 4-bromo-o-xylene. The amount of the phosphite is 1.1 to 1.2 mol based on 1 mol of 3- or 4-bromo-o-xylene. The catalyst can be used in an amount of 0.05 to 0.2 mol based on the 1 mol of 3- or 4-bromo-o-xylene.

The amount of N-bromosuccinimide is 4.0 to 4.5 mol based on 1 mol of the X substituted-o-xylene. The amount of fumaronitrile is 1.0 to 1.3 mol based on 1 mol of the compound [4].

The naphthalocyanine compound [1] wherein M represents 2H, may be prepared by reacting the intermediate [2] in an alcohol in the presence of a proton transferring accelerator. In the reaction, the proton transferring accelerator includes 1,8-diazabicyclo[5,4,0]unde-7-cene, 1,5-diazabicyclo[4,3,0]-5-nonen and the like. The accelerator may be present in an amount of more than stoichiometric amount based on 1 mol of the intermediate. Examples of the alcohols are n-butanol, n-amyl alcohol, 2-methoxyethyl alcohol, 2-ethoxyethyl alcohol and the like. The amount of the alcohol is not limited, but preferably used in an amount of 500 to 2,000 ml, preferably about 1,000 ml. The obtained naphthalocyanine compound wherein M is 2H and $R^1$ and $R^2$ respectively show an alkoxy group, i.e. tetrakis(dialkoxyphosphoryl) naphthalocyanine, may be hydrolyzed with hydrochloric acid etc. to form the naphthalocyanine compound [1] wherein M is 2H and $R^1=R^2=OH$.

The naphthalocyanine compound [1] wherein M represents a metal atom, a metal oxide residue or a metal chloride residue, may be prepared by reacting the intermediate [2] with a metal, a metal oxide or a metal chloride under molten conditions or in a high boiling point solvent. Examples of the metals are Cu, Zn, Ni, Co, Fe, Ge, Sn, Pb, Ti, Cr, Mn, Al, In and the like. Examples of the metal chlorides are CuCl, $Cu_2Cl_2$, $SnCl_2$, $InCl_3.4H_2$, $AlCl_3$, $TiCl_4$, $SiCl_4$, $GeCl_2$, $FeCl_3$, $SnCl_4$ and the like. Examples of the metal oxides are $PbO_2$, PbO and the like. Examples of the high boiling point solvents are a solvent which has a boiling point of more than 180° C., for example, trichlorobenzene (b.p. 218°-219° C.), quinoline (b.p. 238° C.), chloronaphthalene (b.p. 263° C.), bromonaphthalene (b.p. 289° C.) and the like. The amount of the metal, metal oxide and metal chloride in the reaction process is 0.25 to 2 mol, preferably 0.3 to 0.4 mol based on 1 mol of the intermediate [2]. The amount of the high boiling point solvent is not limited and can be varied by a reaction scale and the like. In the above process, the reaction may be carried out in molten conditions in which the reactants are melted at a temperature of 180° to 220° C. for 3 to 6 hours.

Another process for preparing the naphthalocyanine compound [1] wherein M represents a metal atom, metal oxide resiude or metal chloride residue, comprises reacting a X substituted naphthalene-2,3-dicarboxylic anhydride [6] represented by

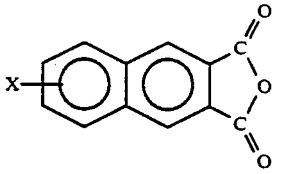

[6]

wherein X is the same as mentioned above, with the metal, the metal oxide or the metal chloride under molten conditions or in a high boiling point solvent in the presence of urea and an optional catalyst. Examples of the catalysts are ammonium molybdate, ammonium vanadate, ammonium arsenate, ammonium phosphate and the like. The other reactants are the same as mentioned above. In the reaction, the amounts of the reactants are 5 to 10 mol for urea, 0.25 or more (preferably 0.3 or more) for the metal, metal oxide or metal chloride and 1,000 to 1,500 ml for the high boiling point solvent, based on 1 mol of the compound [6].

The naphthalocyanine compound [1] wherein M represents a metal atom, a metal oxide residue or a metal chloride residue, comprises reacting a X substituted 1,3 diminobenz (f) isoindoline [7] represented by

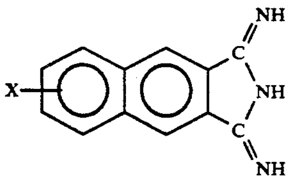

[7]

wherein X is the same as mentioned above, with the metal, the metal oxide or the metal chloride under molten conditions or in a high boiling point solvent in the presence of a tirtiary amine. Examples of the tirtiary amines are trimethylamine, triethylamine, tri-n-butylamine, triethanolamine, tri-n-butanolamine and the like. The other reactants are the same as mentioned above. In the reaction, the amounts of the reactants are 0.25 to 2 mol (preferably 0.3 to 0.4 mol for the metal, metal oxide or metal chloride, a catalyst amount for the tirtiary amine and 100 to 2,000 ml (preferably 500 to 1,000 ml) for the high boiling point solvent.

The naphthalocyanine compound of the present invention is highly soluble in an organic solvent including a polar solvent, such as alcohols, ketones, ethers, esters, aliphatic halogenated hydrocarbons and aromatic hydrocarbons. It therefore can be easily coated by spray, roll, dipping and spinning to form a uniform coating layer without dissolving the substrate. It also absorbs the light of near infrared region, especially 780 to 830 nm which is used for AlGaAs semiconductor laser. The compound is very stable to light, heat, acid, alkali and the like. Other special features of the naphthalocyanine compound are that the absorption characteristics of an electric spectrum are changed by a sort of an organic solvent. For example, tetrakis(diphenylphosphoryl)-naphthalocyanine has an absorption characteristics as shown in FIG. 8 in chloroform, but it is changed to the chart of FIG. 18 in tetrahydrofuran.

EXAMPLES

The present invention is illustrated by the following Examples which, however, are not construed as limiting the present invention to their details.

EXAMPLE 1

Preparation of 4-Diphenylphosphoryl-O-Xylene

A reaction vessel was charged with 100 ml of tetrahydrofuran (THF) which had been dried with lithium aluminum hydride, to which 2.83 g (0.1209 mol) of turning magnesium was added. With refluxing, a dried THF solution of 19.6 g (0.106 mol) of 4-bromo-o-xylene was added dropwise over one hour. After the completion of the addition, it was refluxed for about one hour and then cooled to 5° to 10° C. at which a dried THF solution of 25 g (0.106 mol) of chlorodiphenylphosphine oxide was added dropwise over about 3 hours. After the completion of the addition, it was mixed at 50° to 60° C. for 2 hours and allowed to stand for cooling. Then, 100 ml of dilute hydrochloric acid and 100 ml of diethyl ether were added to the resultant solution and mixed for 30 minutes. It was then extracted three time with 200 ml of diethyl ether. The extracted solution was rinsed three times with a 5% sodium hydrogencarbonate solution and dried with anhydrous sodium sulfate. The ether solution was condensed and subjected to column chromatography to obtain 25 g of white solid which had a chart (FIG. 1) of NMR spectrum in $CDCl_3$ to find the following chemical structure;

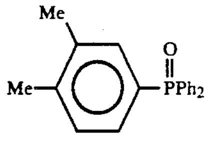

δ Value 7.45 (13H, br)
2.23 (6H, br-s)

EXAMPLE 2

Preparation of 3-Diethoxyphosphoryl-O-Xylene

A mixture solution of 25.0 g (0.135 mol) of 3-bromo-o-xylene and 2.0 g (0.015 mol) of anhydrous nickel chloride was heated to 150° to 160° C., to which 26.9 g (0.162 mol) of triethyl phosphate was added for 1 to 2 hours. After the completion of the addition, it was mixed at that temperature and then cooled. To the cooled solution, 30 ml of water was added and mixed for another 30 minutes. It was then extracted three time with 100 ml of diethyl ether. The extracted solution was rinsed three times with a 5% sodium hydrogencarbonate solution and dried with anhydrous sodium sulfate. The ether solution was condensed and subjected to column chromatography to obtain 20 g of transparent liquid which had a chart (FIG. 2) of NMR spectrum in $CDCl_3$ to find the following chemical structure;

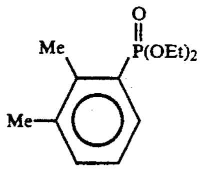

δ Value 7.92–7.13 (3H, m)
4.13 (4H, d.q., $J_{H-H} = J_{H-P} = 7.26$ Hz)
2.50 (3H, s)
2.30 (3H, s)
1.33 (6H, t, $J_{H-H} = 7.26$ Hz)

EXAMPLE 3

Preparation of 4-Diethoxyphosphoryl-O-Xylene

Transparent liquid of 20.8 g was obtained as generally described in Example 2, with the exception that 4-bromo-o-xylene was employed instead of 3-bromo-o-xylene. It had a chart (FIG. 3) of NMR spectrum in $CDCl_3$ to find the following chemical structure;

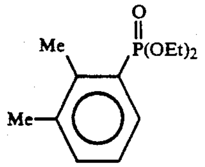

δ Value 7.66–7.28 (3H, m)
4.11 (4H, d.q., $J_{H-H} = J_{H-P} = 7.04$ Hz)
2.30 (6H, s)
1.32 (6H, t, $J_{H-H} = 7.04$ Hz)

EXAMPLE 4

Preparation of 6-Diphenylphosphoryl-2,3-Dicyano NAPHTHALENE

A reaction vessel was charged with 100 ml of carbon tetrachloride in which 10.3 g (0.035 mol) of 4-diphenylphosphoryl-o-xylene and 25.3 g (0.142 mol) of N-bromosuccinimide were dissolved. Then, 0.3 g of benzoyl peroxide was added and irradiated by a mercury lamp with refluxing for 10 to 12 hours. After cooling, the precipitated white solid was filtered off and the filtrate was condensed under reduced pressure. The obtained solid was rinsed with a small amount of methanol, and then dried to obtained 21.3 g of 1,2-bis(dibromomethyl)-4-diphenylphosphoryl benzene. Its analysis showed as follow;

(1) Elemental analysis: Calculated value (%) C; 38.61, H; 2.41, Measured value (%) C; 37.97, H; 2.39.

(2) NMR spectrum in $CDCl_3$: δ Value 8.28-7.39 (13H, m), 7.26 (1H, s), 7.06 (1H, s), Next, 21.3 (0.034 mol) of the obtained 1,2-bis(dibromomethyl-4diphenylphosphoryl benzene and 3.5 g (0.045 mol) of fumaronitrile were dissolved in 100 ml of anhydrous N,N-dimethylformamide, to which 23.2 g (0.155 mol) of sodium iodide was added with stirring and mixed at about 75° C. in a nitrogen atmosphere for another 5 hours. After finishing the reaction, the reaction solution was poured in about 500 ml of ice and water and mixed for about 50 minutes. Sodium hydrogensulfite was added thereto until the solution turned to light yellow, and then mixed for about one hour. The precipitated light yellow solid was filtered out and rinsed with water. The solid was dried under reduced pressure to obtain crude solid of 8.5 g.

The crude solid of 7.0 g was recrystallized from ethanol to obtain white crystal of 5.85 g. The crystal was identified as 6-diphenylphosphoryl-2,3-dicyano naphthalene by the following analysis;

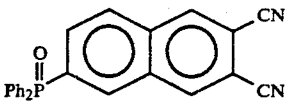

(1) Elemental analysis: Calculated value (%) C; 76.19, H; 3.97, N; 7.41,Measured value (%) C; 75.53, H; 4.11, N; 7.45.

(2) NMR spectrum in $CDCl_3$ (FIG. 4): δ Value 8.46 - 7.41 (15H, m).

(3) IR spectrum (thin layer method of $CHCl_3$ solution) (FIG. 5): 2,200 $cm^{-1}$ (an absorption derived from C≡N); 1,210 $cm^{-1}$, 1,175 $cm^{-1}$ (an absorption derived from $Ph_2P$=O).

EXAMPLE 5

Preparation of 6-Diethoxyphosphoryl-2,3-Dicyano Naphthalene

A reaction vessel was charged with 500 ml of carbon tetrachloride in which 47.7 g (0.197 mol) of 4-diethoxyphosphoryl-o-xylene and 144 g (0.809 mol) of N-bromosuccinimide were dissolved. Then, 1.0 g of benzoyl peroxide was added and irradiated by a mercury lamp with refluxing for 10 to 12 hours. After cooling, the precipitated white solid was filtered off and the filtrate was condensed under reduced pressure. The obtained viscous liquid was mixed with a small amount of an ether and subjected to a ultrasonic to precipitate solid. The solid was filtered to obtain 40 g of white solid. The solid was identified as 1,2-bis(dibromomethyl)-4-diethoxyphosphoryl benzene by the following analysis;

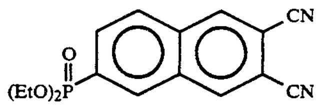

(1) Elemental analysis: Calculated value (%) C; 27.82, H; 2.90, Measured value (%) C; 26.25, H; 2.68.

(2) NMR spectrum in $CDCl_3$: δ Value 8.12 - 7.76 (3H, m), 7.23 (1H, s), 7.07 (1H, s), 4.17 (4H, d.q., $J_{H-H}=J_{H-P}$=7.26 Hz), 1.36 (6H, t, $J_{H-H}$=7.26 Hz).

Next, 20.0 (0.036 mol) of the obtained 1,2-bis(dibromomethyl)-4-diethoxyphosphoryl benzene and 3.5 g (0.045 mol) of fumaronitrile were dissolved in 100 ml of N,N-dimethylformamide, to which 23.2 g (0.155 mol) of sodium iodide was added with stirring and mixed at about 75° C. in a nitrogen atmosphere for another 5 hours. After finishing the reaction, the reaction solution was slowly poured into 2,000 ml of a 5% sulfurous acid solution to produce white slurry. After the completion of pouring, salt was precipitated with sodium chloride and filtered out and rinsed with water. The solid was dried under reduced pressure to obtain solid of 5.1 g. The solid was identified as 6-diethoxyphosphoryl-2,3-dicyano naphthalene by the following analysis;

(1) Elemental analysis: Calculated value (%) C; 61.15, H; 4.78, N; 8.92, Measured value (%) C; 60.09, H; 4.76, N; 8.89.

H: (2) NMR spectrum in $CDCl_3$ (FIG. 6): δ Value 8.61 (1H, s), 8.45 (1H, s), 8.41 (1H, s), 8.12 (1H, s), 8.04 (1H, s), 4.19 (4H, d.q., $J_{H-H}=J_{H-P}$=7.04 Hz), 1.36 (6H, t, $J_{H-H}$=7.04 Hz).

(3) IR spectrum (thin layer method of $CHCl_3$ solution) (FIG. 7):

2,250 $cm^{-1}$ (an absorption derived from C≡N) 1,290 $cm^{-1}$, 1,260 $cm^1$ (an absorption derived from $(C_2H_5O)_2$ P=O).

EXAMPLE 6

Preparation of Tetrakis(Diphenylphosphryl)Naphthalocyanine

A mixture of 1.124 g (3 mmol) of 6-diphenylphosphoryl-2,3-dicyanonaphthalene and 3 ml of dried amyl alcohol was heated to reflux in a nitrogen atmosphere, to which 0.5 ml (3.3 mmol) of 1,8-diazabicyclo[5,4,0]undec-7-cene was added dropwise for about 15 minutes. It was mixed with refluxing for about 10 hours, and then cooled to about 70° C. After adding 30 ml of methanol to the mixture, it was mixed for one hour. Dark green solid was precipitated and filtered, followed by rinsing with methanol. The solid was then dispersed in 300 ml methanol and heated to reflux for about one hour. It was filtered under vacuum at an elevated temperature and rinsed with methanol until filtrated methanol was transparent. The obtained dark green solid was dried under reduced pressure to obtain 600 mg of solid. The solid was identified as tetrakis(diphenylphosphoryl)-naphthalocyanine by the following analysis;

(1) Elemental analysis: Calculated value (%) C; 76.09, H; 4.10, N; 7.40, Measured value (%) C; 72.80, H; 4.33, N; 7.23.

(2) Electron spectrum in $CHCl_3$ (FIG. 8); Electron spectrum in THf (FIG. 18).

(3) IR spectrum (KBr method) (FIG. 9)

EXAMPLE 7

Preparation of Tetrakis(Diethoxyphosphoryl)Naphthalocyanine

A reaction was conducted with 1.2 g (4.7 mmol) of 6-diethoxyphosphoryl-2,3-dicyanonaphthalene, 3 ml of dried amyl alcohol and 0.8 ml (5.3 mmol) of 1,8-diazabicyclo[5,4,0]unde-7-cene as generally described in Example 6. After the completion of the reaction, 5 ml of water and 5 ml of methanol were added and mixed, and salted out with sodium chloride. The obtained solid was filtered and rinsed with water. It was rinsed with a mixture of 3/7 of methanol/water until filtrate was transparent. The obtained dark green solid was dried under reduced pressure to obtain 450 mg of solid. The solid was identified as tetrakis(diethoxyphosphoryl)-naphthalocyanine by the following analysis;

(1) Elemental analysis: Calculated value (%) C; 61.05, H; 4.93, N; 8.90, Measured value (%) C; 60.92, H; 4.90, N; 8.87.

(2) Electron spectrum in $CHCl_3$ (FIG. 10)

(3) IR spectrum (KBr method) (FIG. 11)

EXAMPLE 8

Preparation of Tetrakis(Dihydroxyphosphoryl)Naphthalocyanine

A mixture of 100 mg of tetrakis(diethoxyphosphoryl)naphthalocyanine and 100 ml of a 10% hydrochloric acid was heated to reflux for about 5 hours and then allowed to cool to obtain dark green solid. The obtained solid was rinsed with about 50 ml of methanol and dried under reduced pressure to obtain about 55 mg of solid. The solid was identified as tetrakis(dihydroxyphosphoryl)naphthalocyanine by the following analysis;

(1) Elemental analysis: Calculated value (%) C; 55.71, H; 2.90, N; 10.8, Measured value (%) C; 55.50, H; 2.87, N; 10.75.

(2) Electron spectrum in 5% sodium hydrogencarbonate solution (FIG. 12).

(3) IR spectrum (KBr method) (FIG. 13).

EXAMPLE 9

Preparation of Tetrakis(Diphenylpyosphoryl)Vanadylnaphthalocyanine

A mixture of 1.0 g of 6-diphenylphosphoryl-2,3-dicyanonaphthalene, 0.3 g (1.33 mmol) of vanadium chloride, 0.5 ml of tri-n-butylamine and 3 ml of alpha-bromonaphthalene was mixed at 180° to 200° C. for about 3 hours and then allowed to cool to 60° C. Next, 50 ml of methanol was added and mixed for one hour to precipitate dark green solid. The solid was rinsed with methanol until filtrate was transparent. It was then dispersed in 300 ml of a 3% hydrochloric acid and mixed at 70° to 80° C. for about one hour. After filtering, it was rinsed with water and then rinsed with 300 ml of methanol. The obtained dark green solid was dried under reduced pressure to obtain 525 mg of solid. The solid was identified as tetrakis(diphenylphosphoryl)vanadylnaphthalocyanine by the following analysis;

(1) Elemental analysis: Calculated value (%) C; 73.00, H; 3.80, N; 7.09, Measured value (%) C; 70.13, H; 4.02, N; 6.84.

(2) Electron spectrum in $CHCl_3$ (FIG. 14).

(3) IR spectrum (KBr method) (FIG. 15).

EXAMPLE 10

Preparation of Tetrakis(Diphenylphosphoryl)Chloroindiumnaphthalocyanine

A mixture of 1.5 g (4 mmol) of 6-diphenylphosphoryl)chloroindiumnaphthalocyanine, 0.75 g (2.56 mmol) of indium chloride tetrahydrate and 3 ml of quinoline was mixed at about 200° C. for about 6 hours and allowed to cool to about 60° C., to which 60 ml of methanol was added and mixed for one hour to precipitate dark green solid. The solid was filtered and rinsed with methanol until the filtrate was transparent. It was then dispersed in 300 ml of a 3% hydrochloric acid solution and mixed at 70° to 80° C. for about one hour. After filtering, it was rinsed with water and then rinsed with 300 ml of methanol, followed by drying under reduced pressure to obtain 500 mg of solid. The solid was identified as tetrakis(diphenylphosphoryl)chloroindiumnaphthalocyanine by the following analysis;

(1) Elemental analysis: Calculated value (%) C; 69.30, H; 3.61, N; 6.74, Measured value (%) C; 67.64, H; 3.82, N; 6.41.

(2) Electron spectrum in $CHCl_3$ (FIG. 16).

(3) IR spectrum (KBr method) (FIG. 17).

Figure 1:
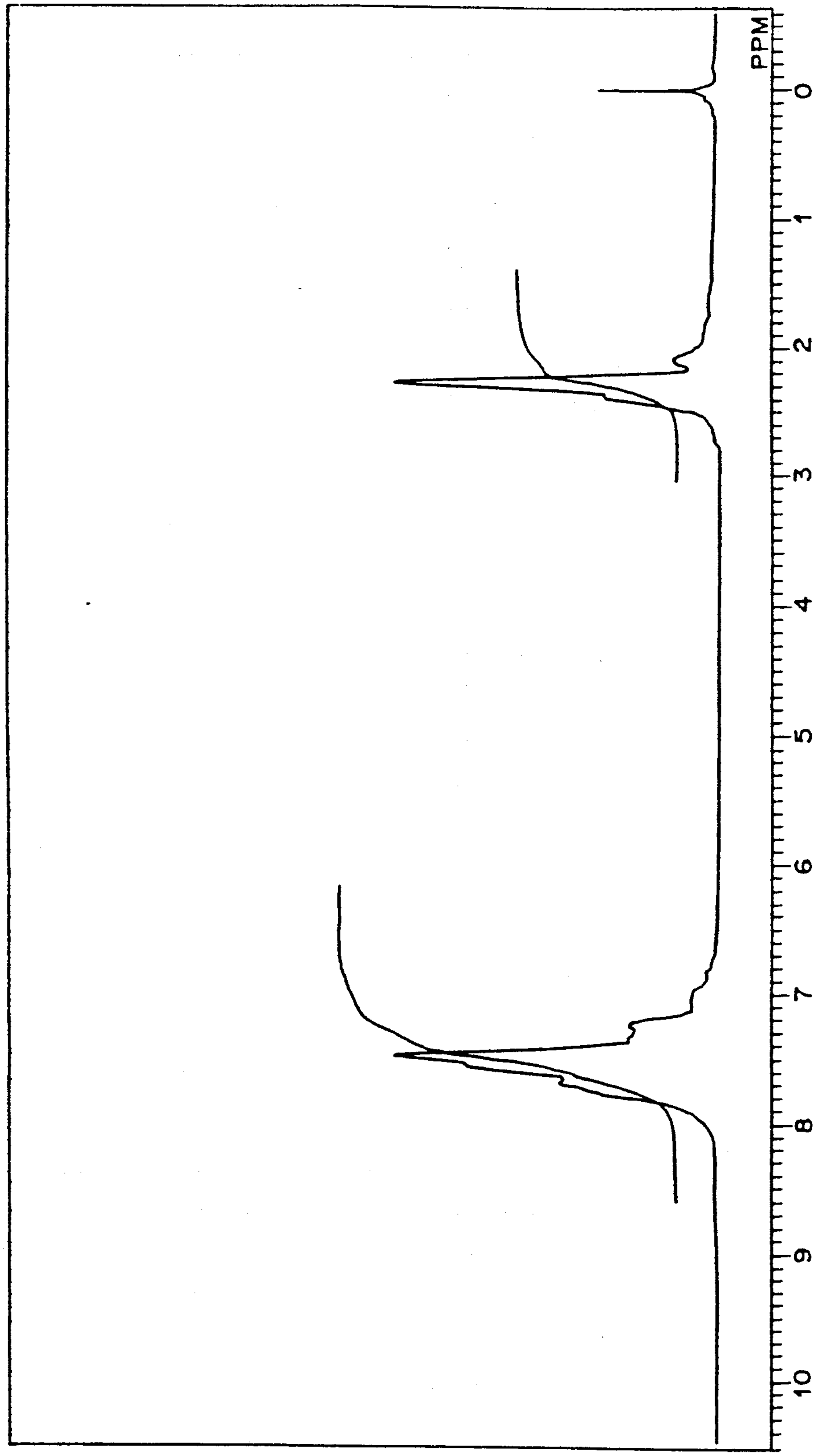
FIG. 1 shows an NMR spectrum of the compound of Example 1.
Figure 2:
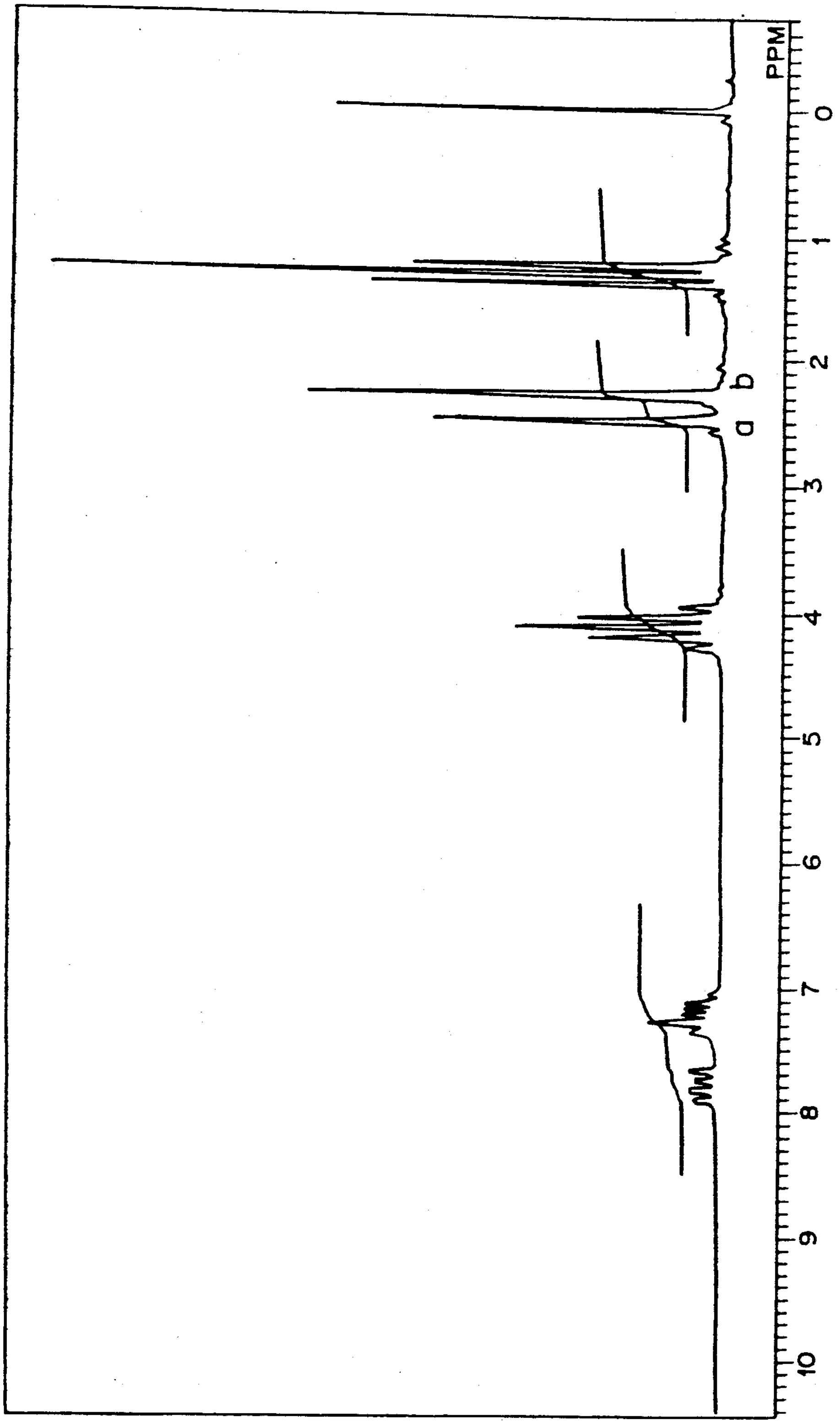
FIG. 2 shows an NMR spectrum of the compound of Example 2.
Figure 3:
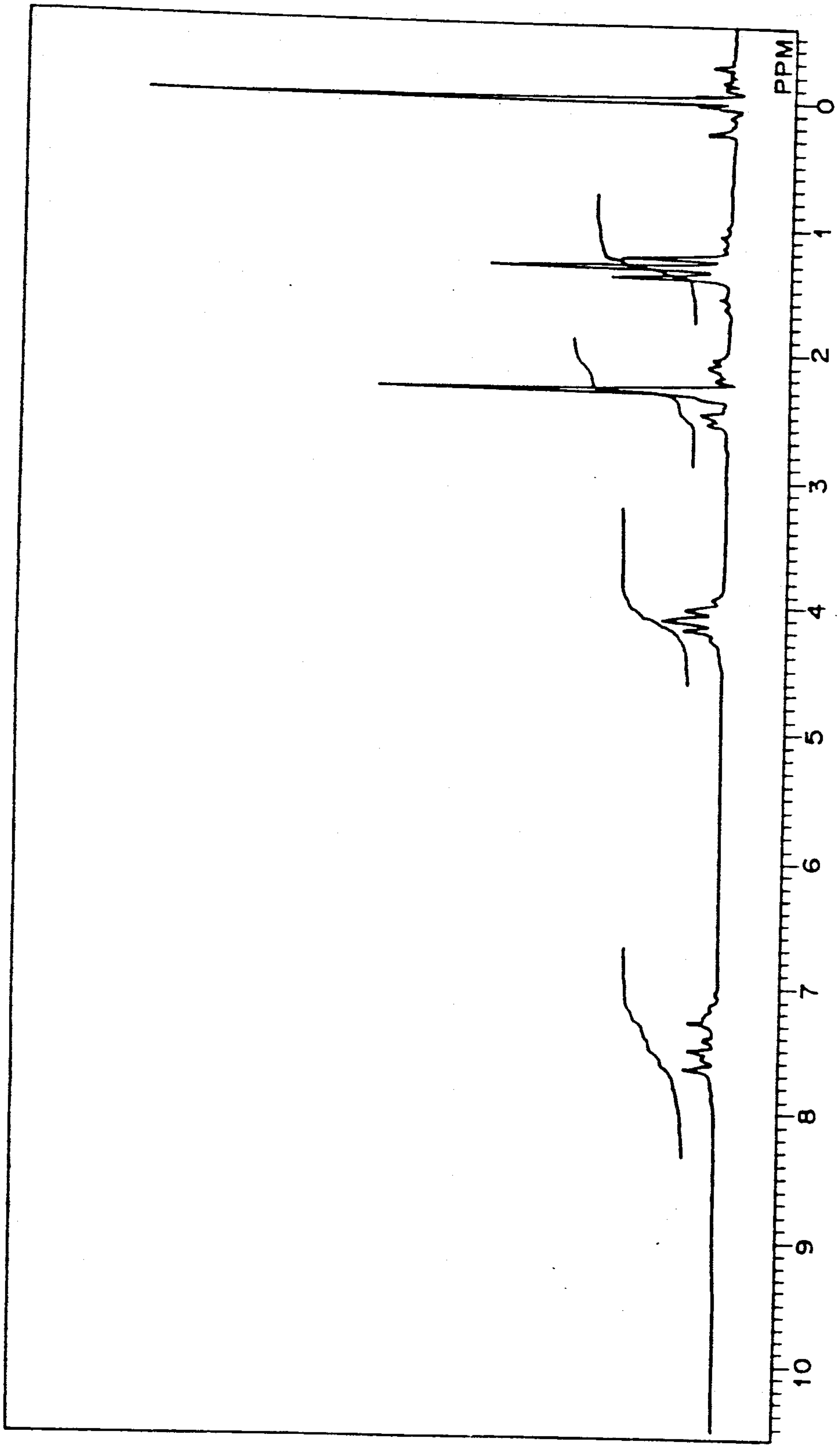
FIG. 3 shows an NMR spectrum of the compound of Example 3.
Figure 4:
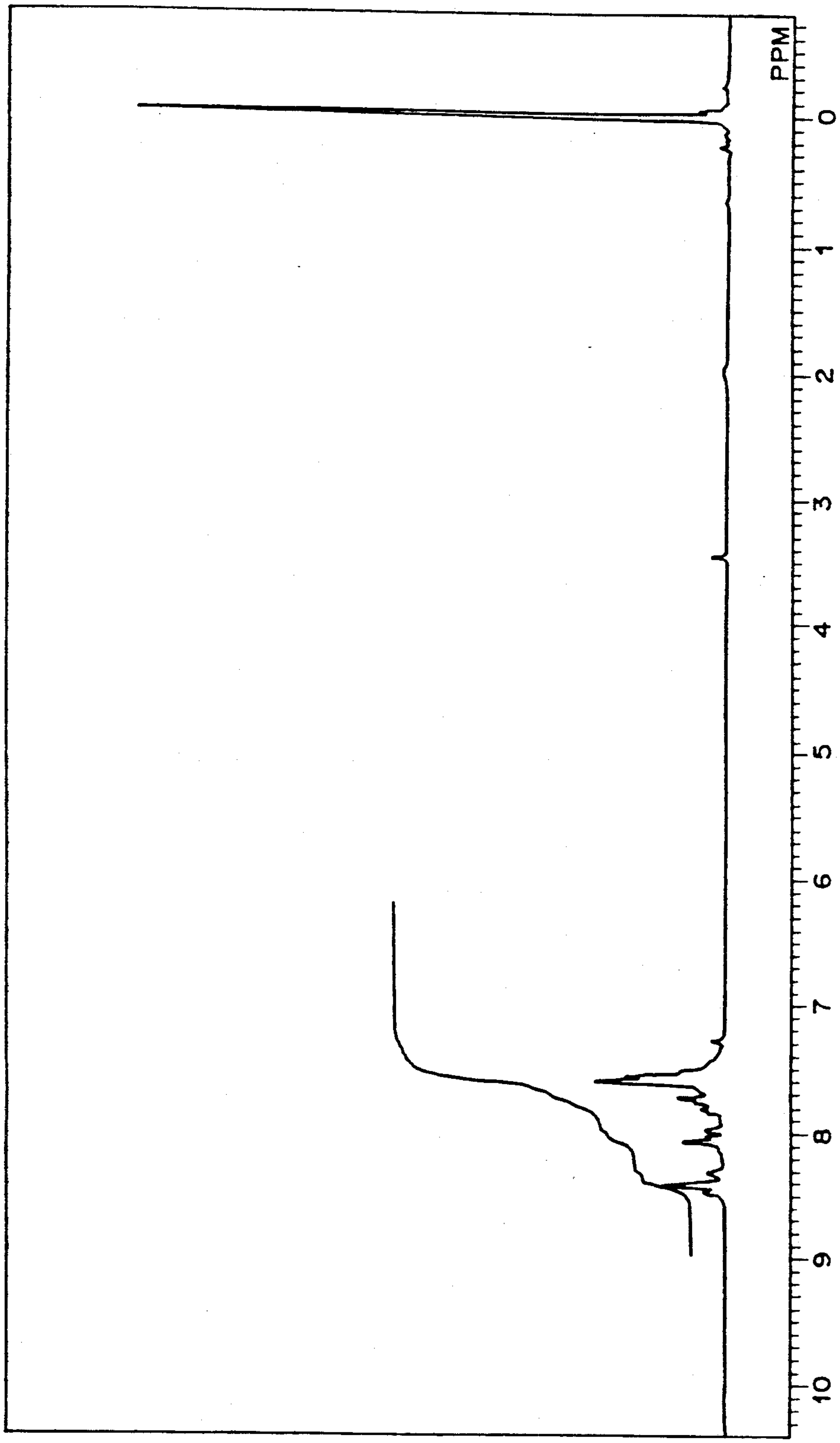
FIG. 4 shows an NMR spectrum of the compound of Example 4.
Figure 5:
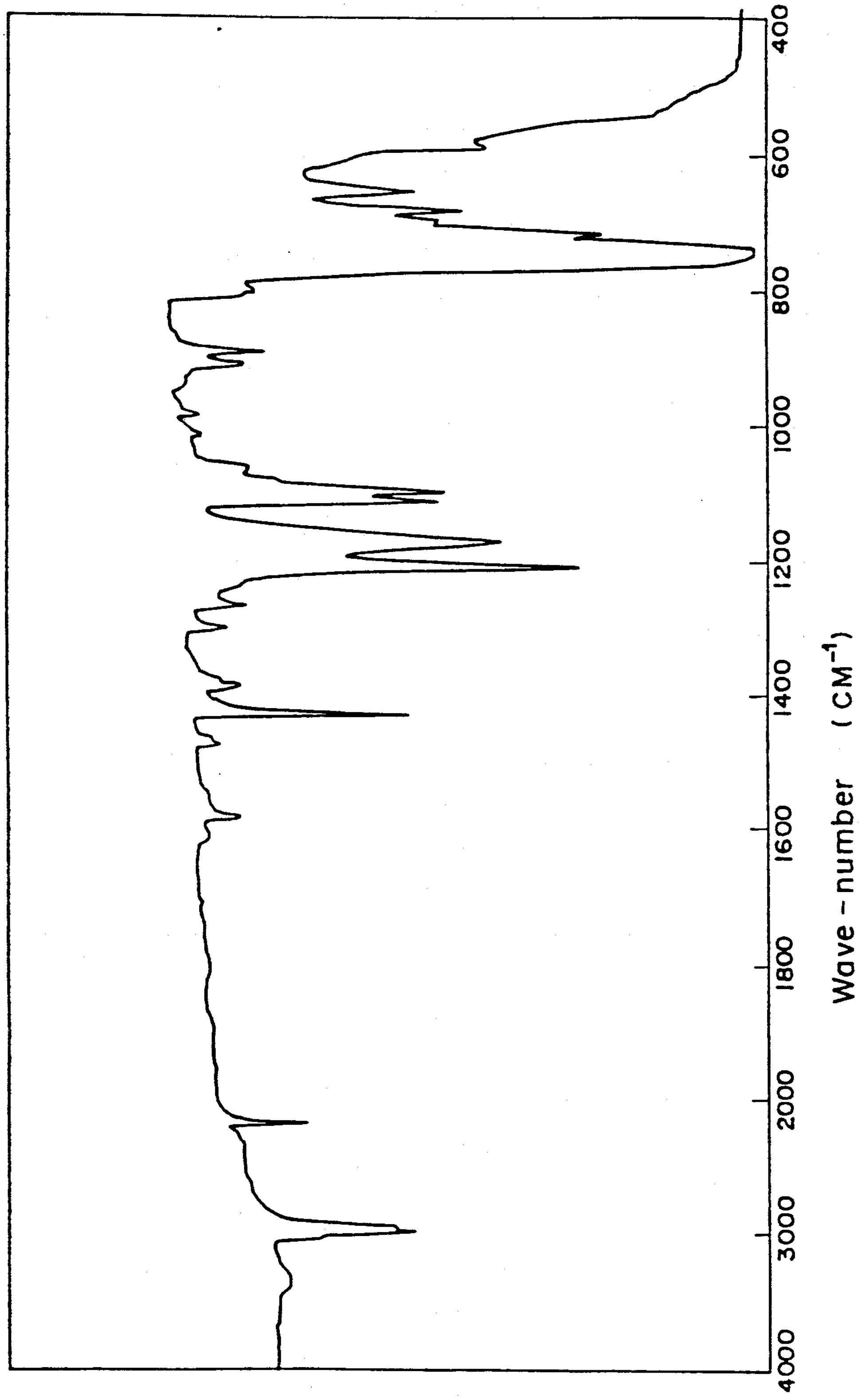
FIG. 5 shows an IR spectrum of the compound of Example 4.
Figure 6:
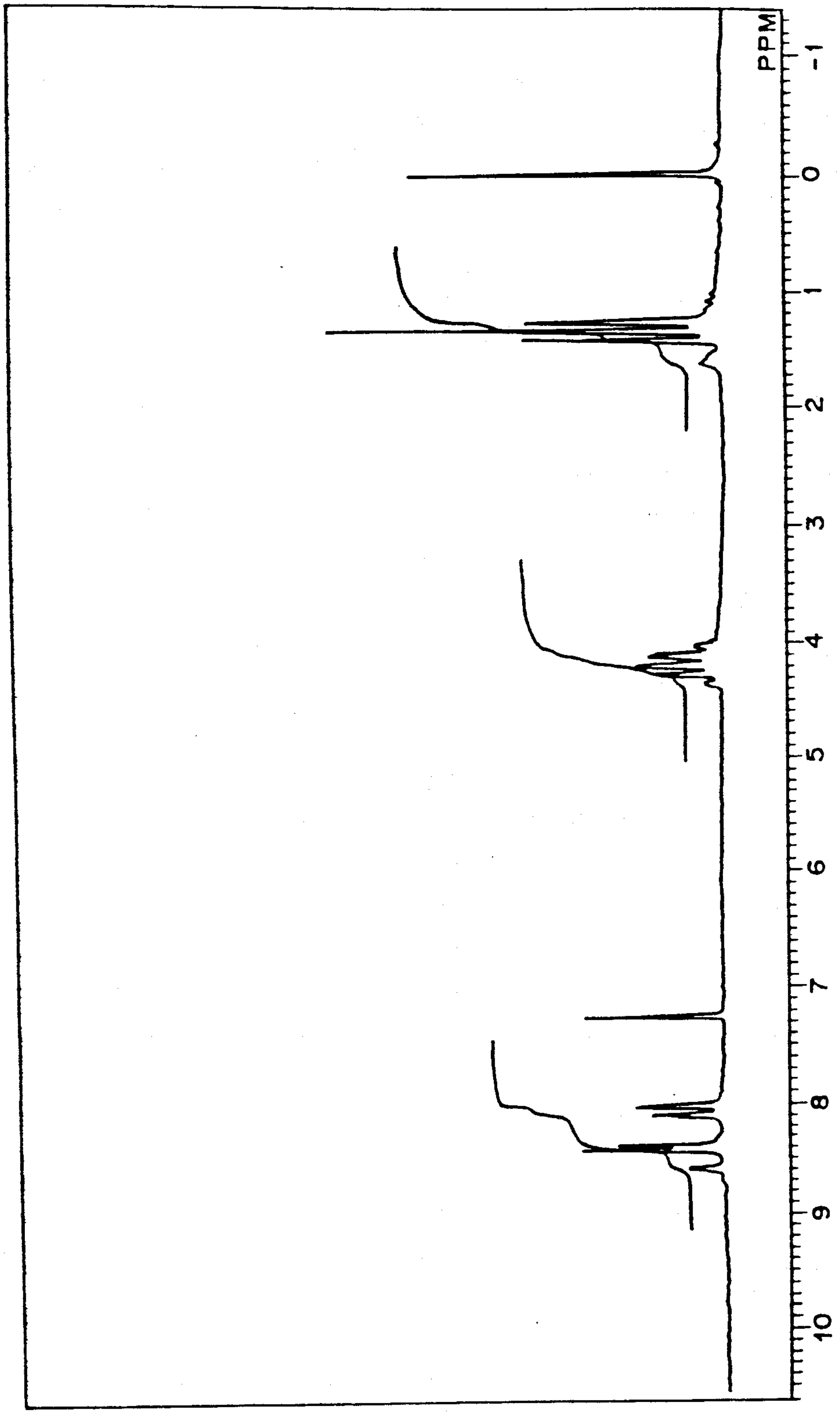
FIG. 6 shows an NMR spectrum of the compound of Example 5.
Figure 7:
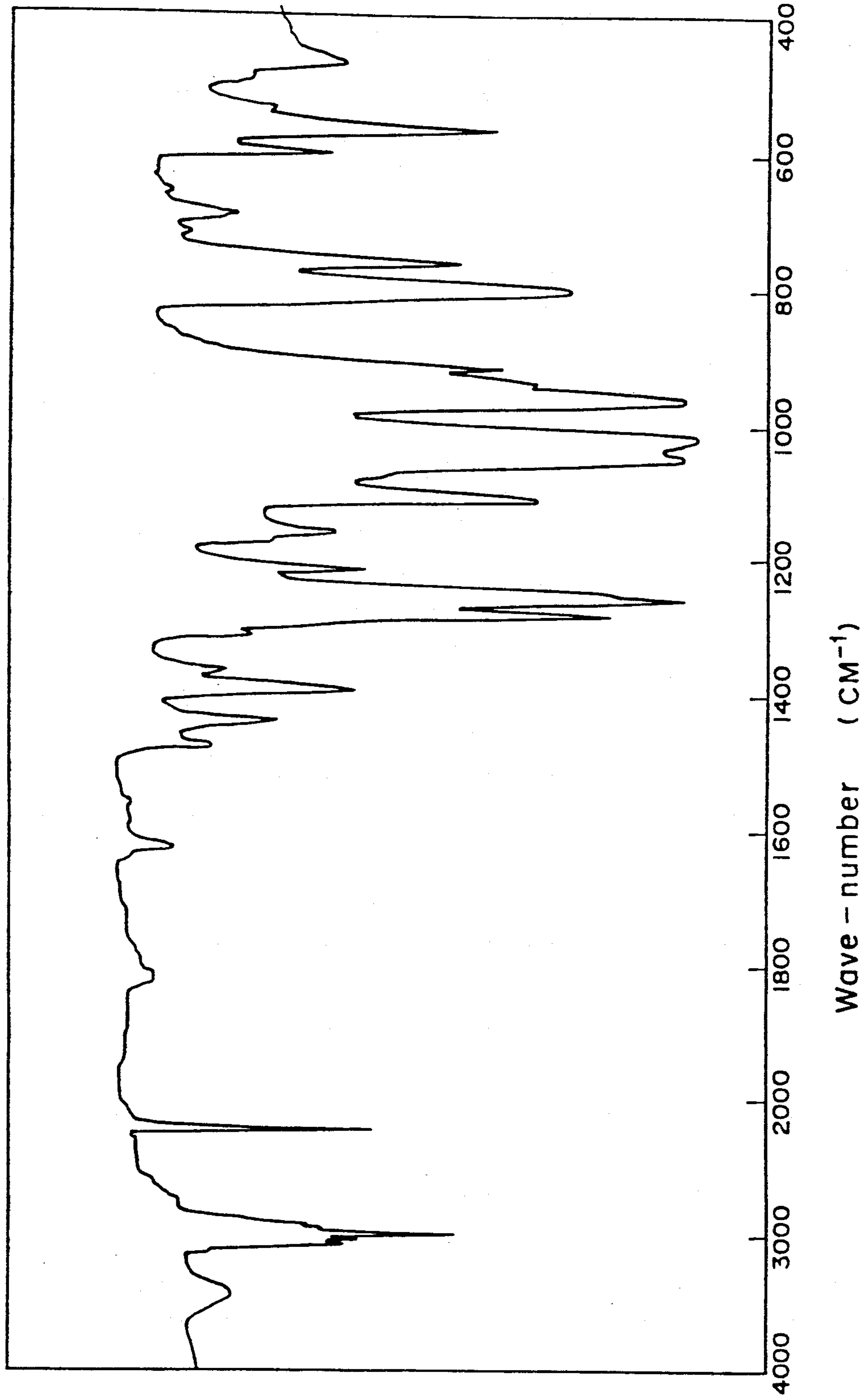
FIG. 7 shows an IR spectrum of the compound of Example 5.
Figure 8:
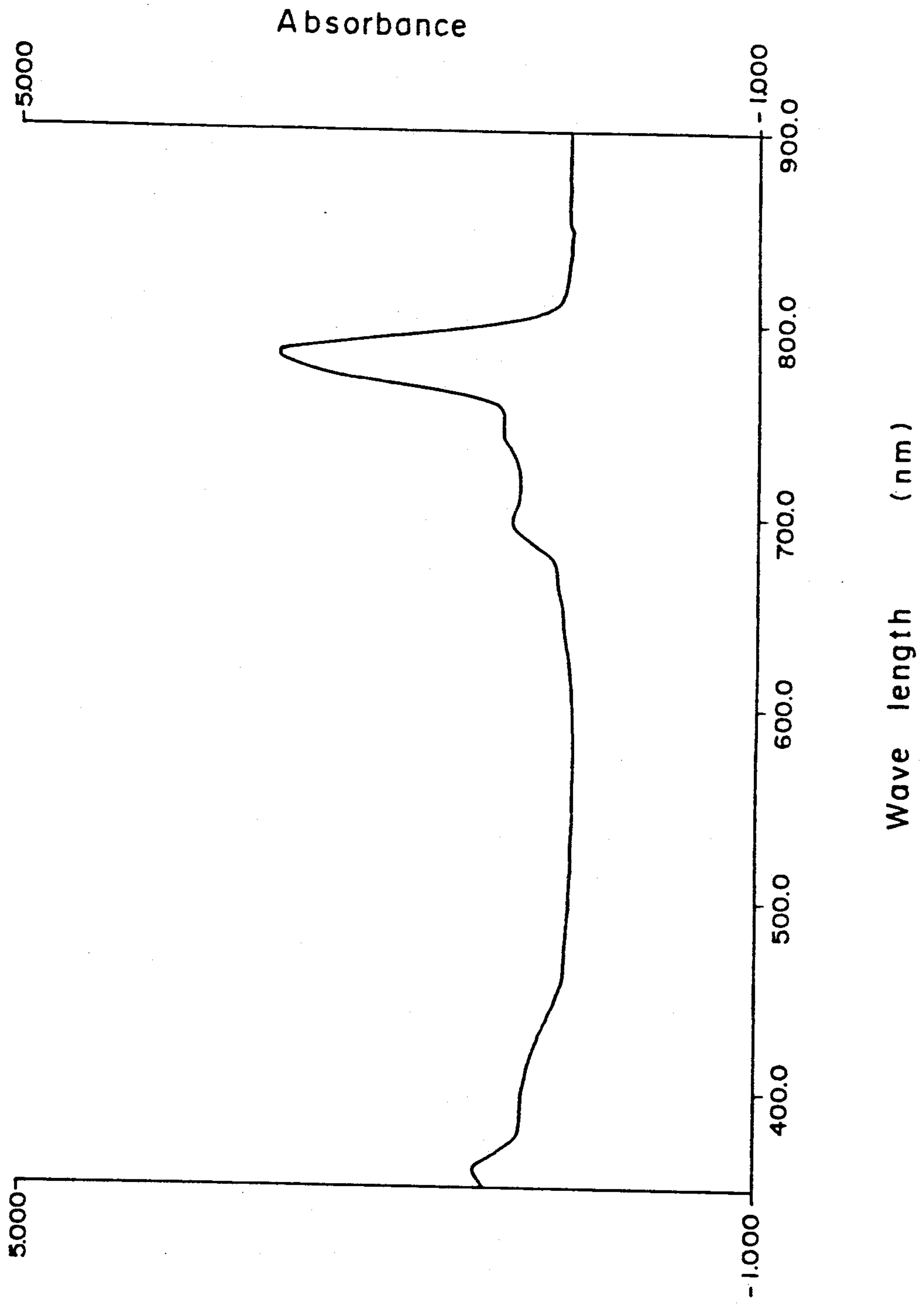
FIG. 8 shows an electron spectrum of the compound of Example 6.
Figure 9:
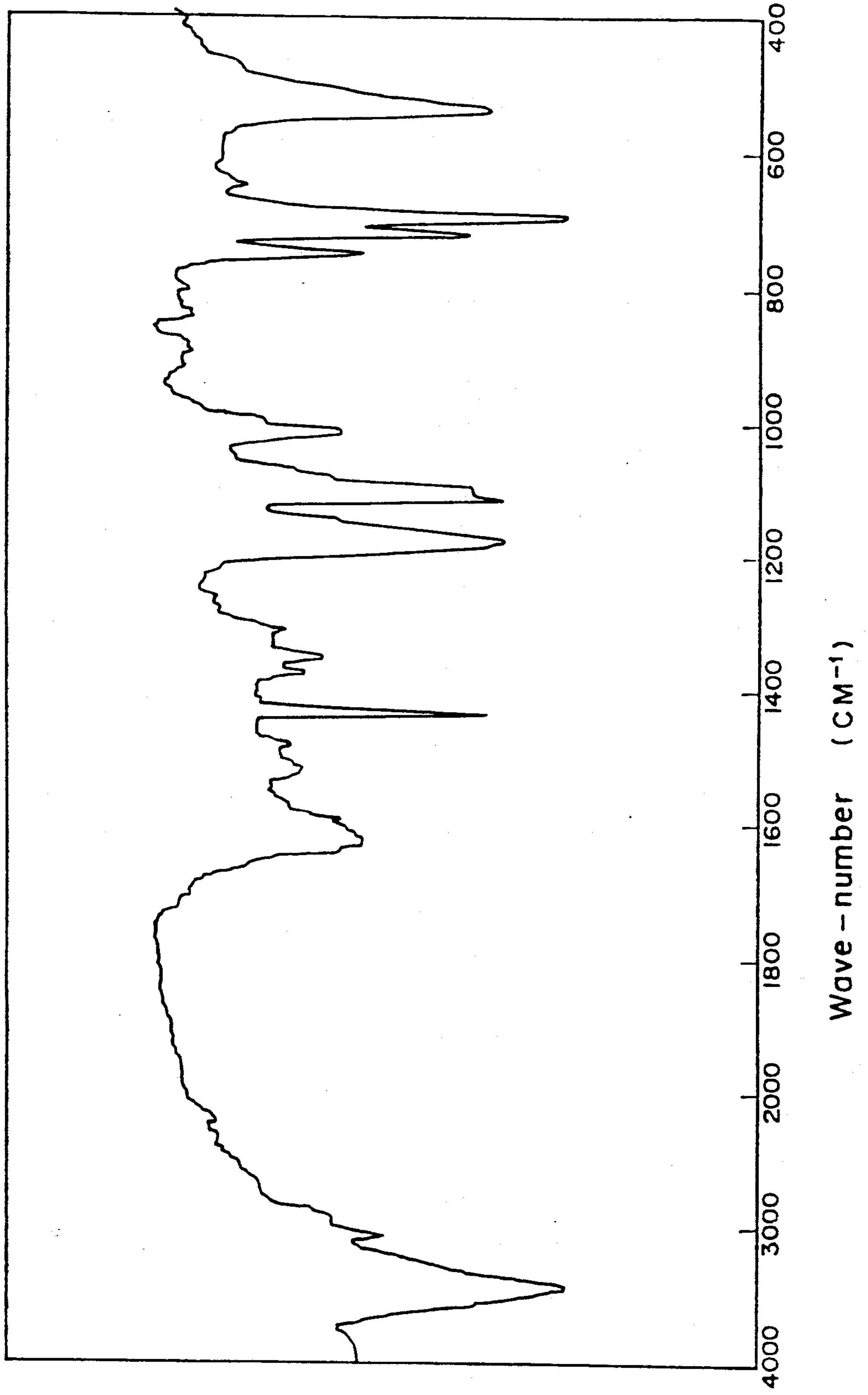
FIG. 9 shows an IR spectrum of the compound of Example 6.
Figure 10:
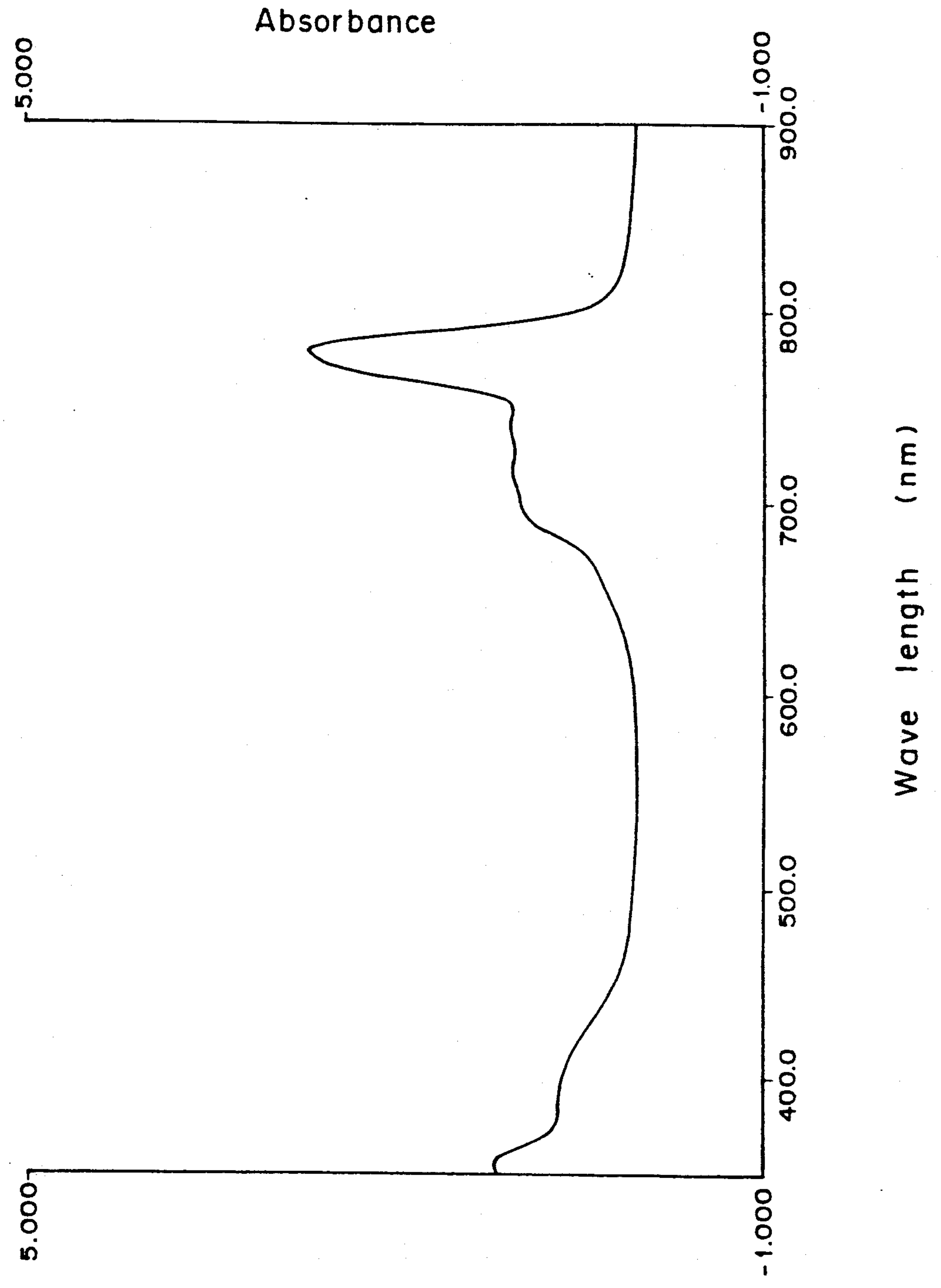
FIG. 10 shows an electron spectrum of the compound of Example 7.
Figure 11:
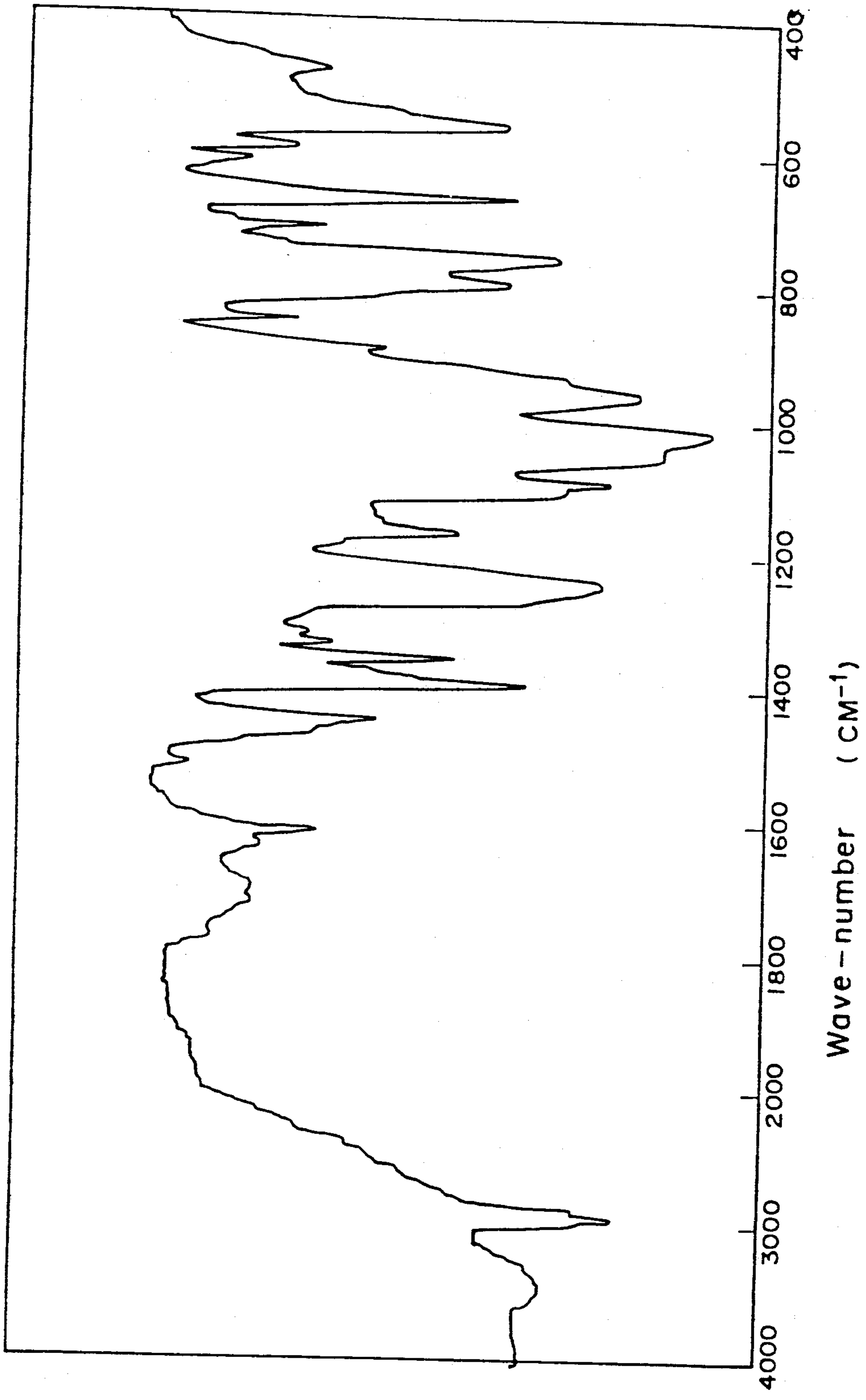
FIG. 11 shows an IR spectrum of the compound of Example 7.
Figure 12:
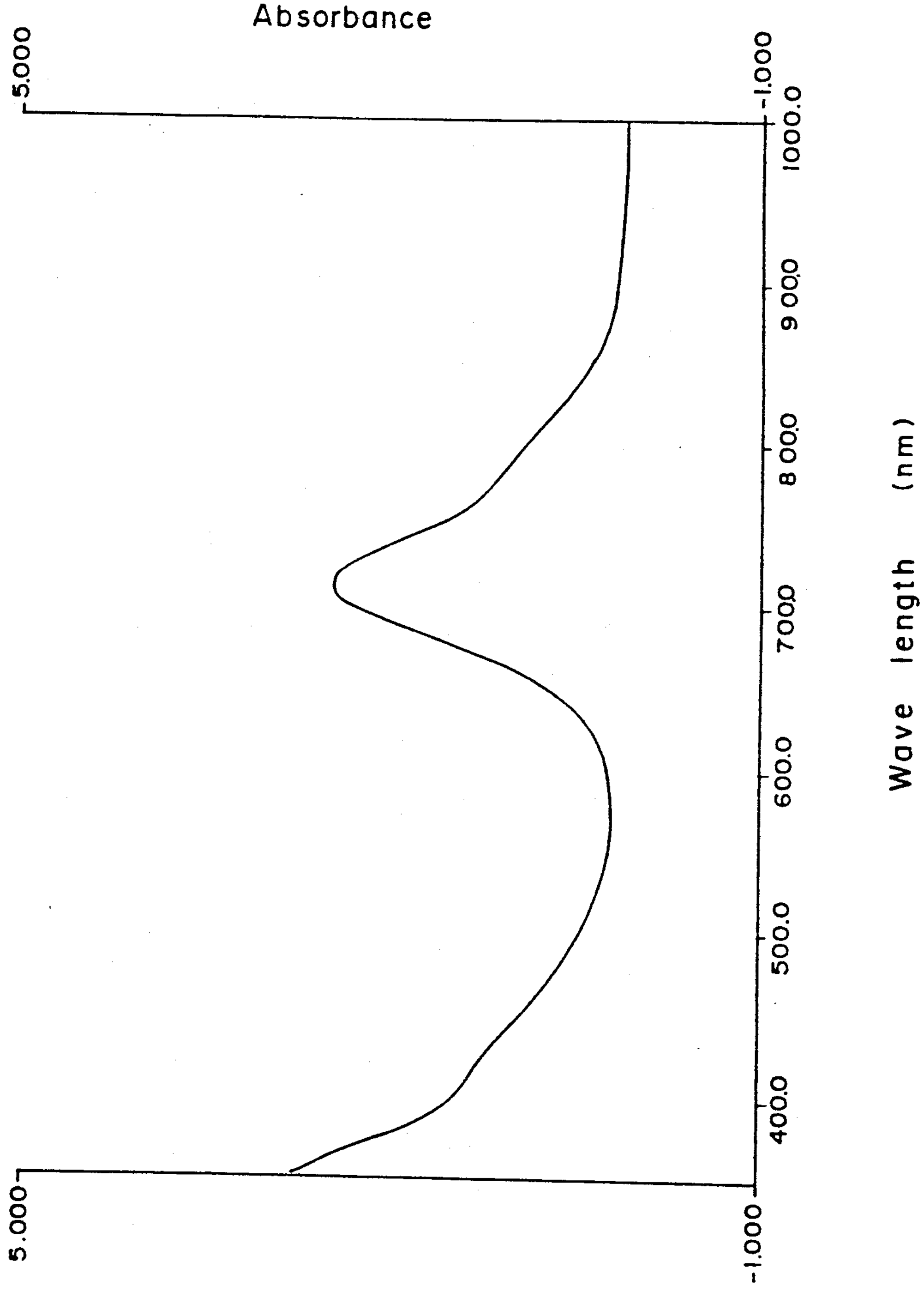
FIG. 12 shows an electron spectrum of the compound of Example 8.
Figure 13:
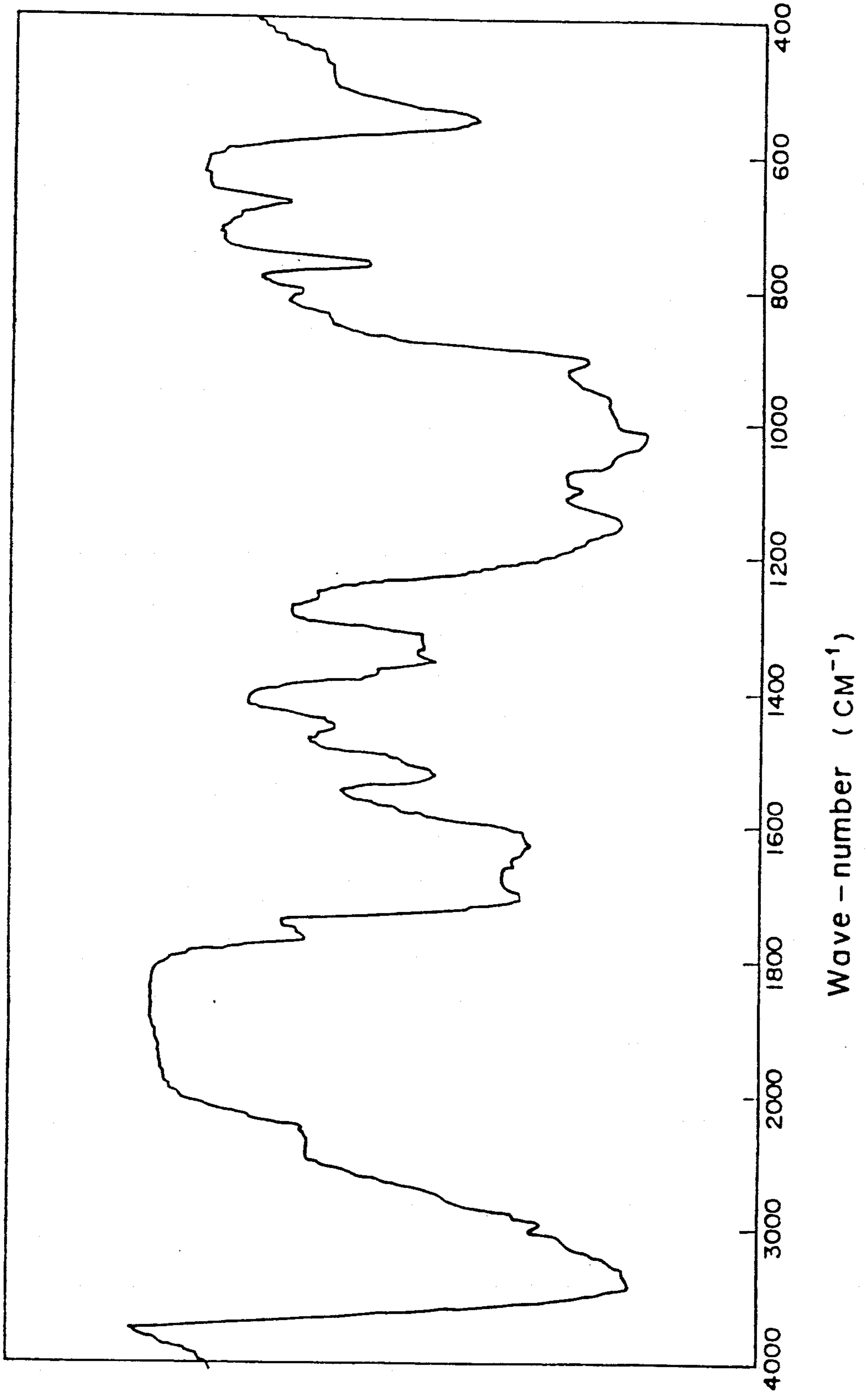
FIG. 13 shows an IR spectrum of the compound of Example 8.
Figure 14:
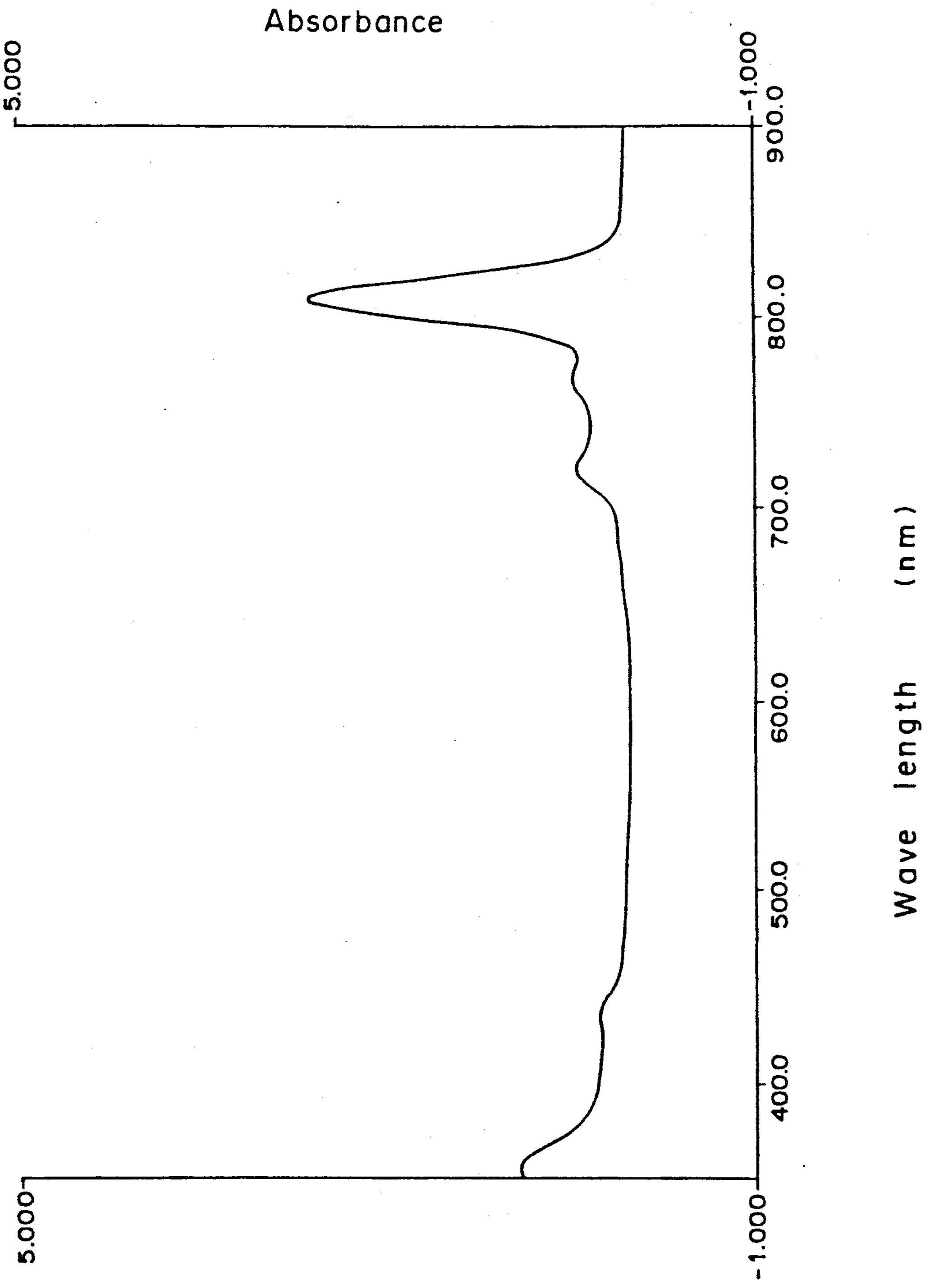
FIG. 14 shows an electron spectrum of the compound of Example 9.
Figure 15:
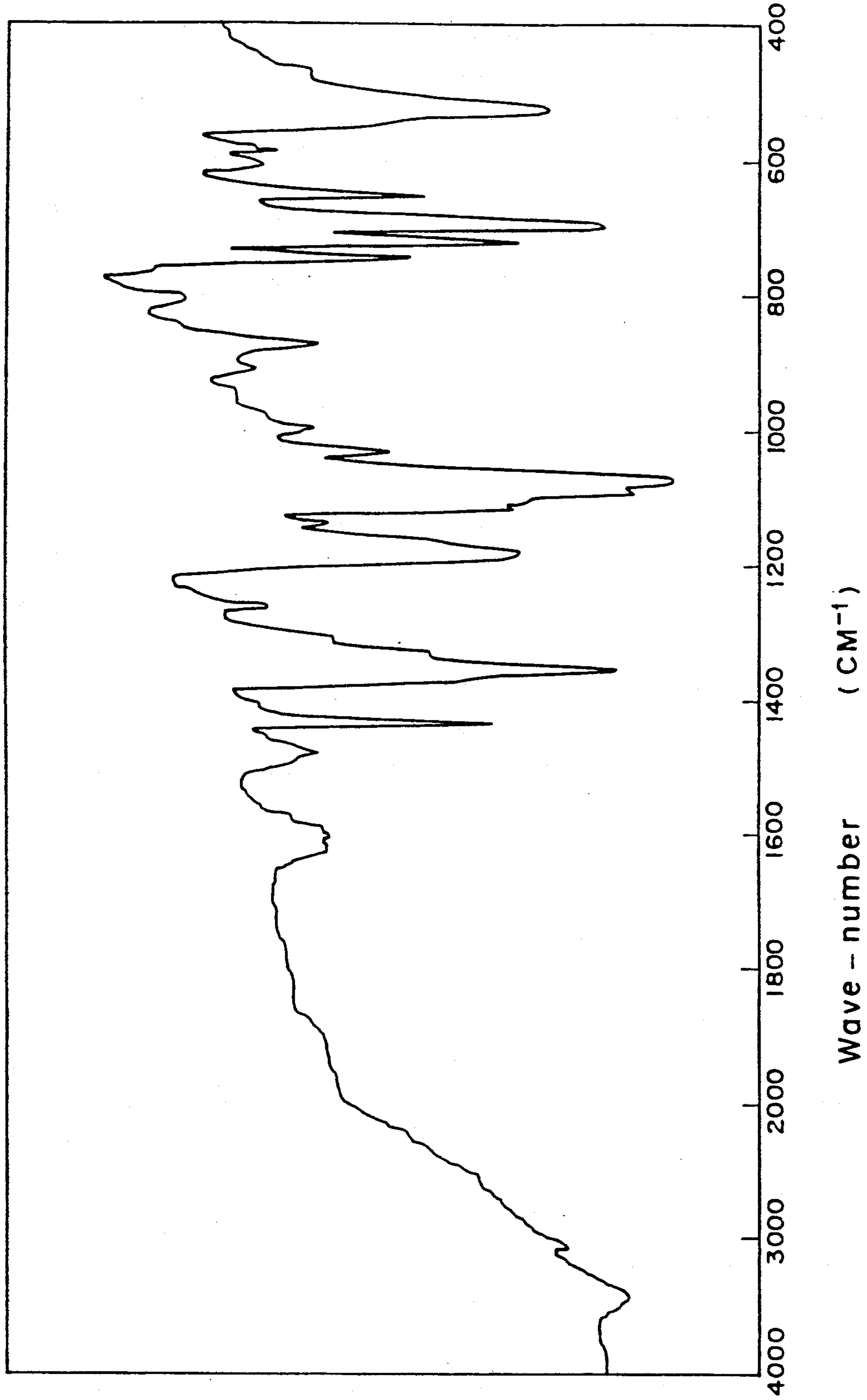
FIG. 15 shows an IR spectrum of the compound of Example 9.
Figure 16:
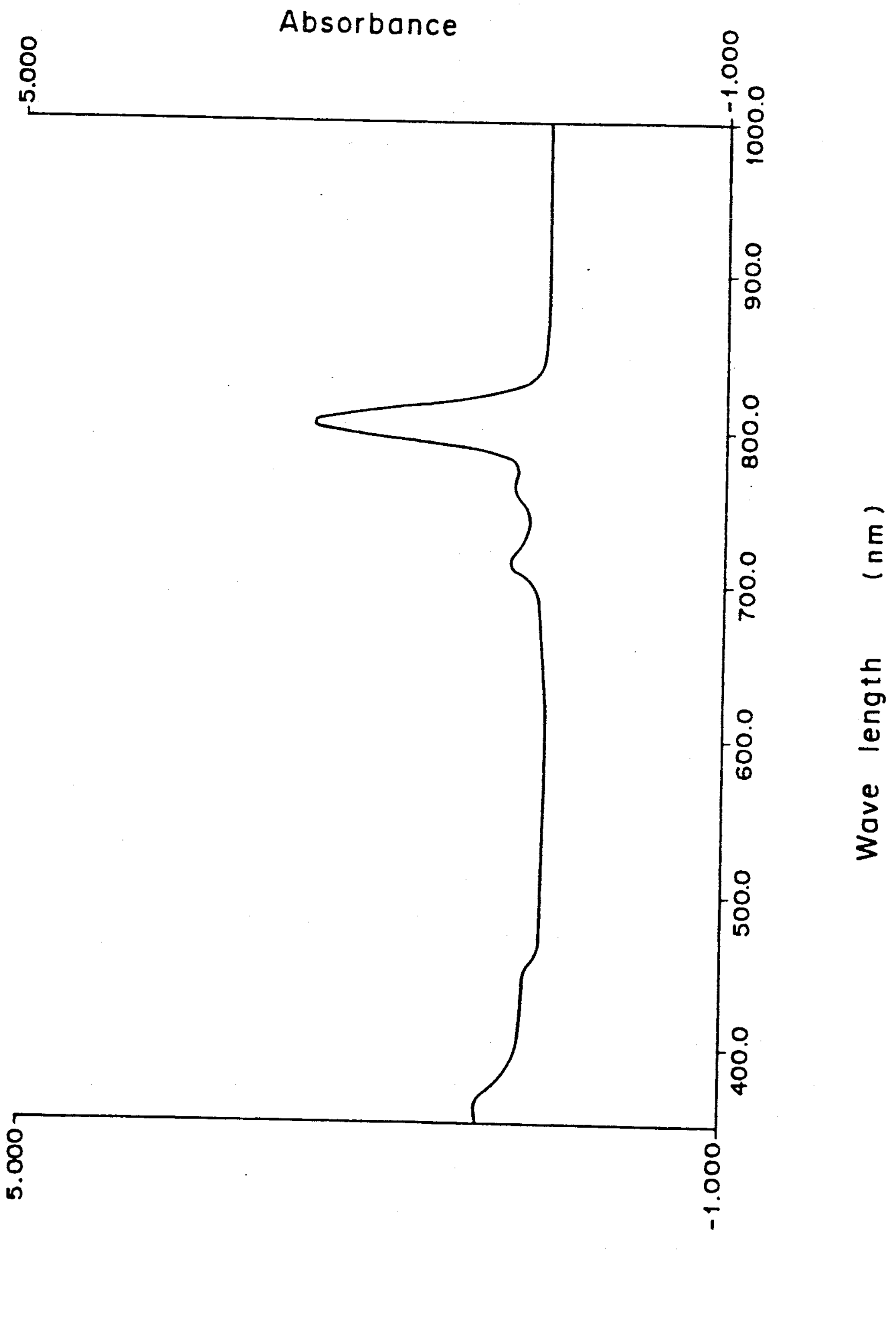
FIG. 16 shows an electron spectrum of the compound of Example 10.
Figure 17:
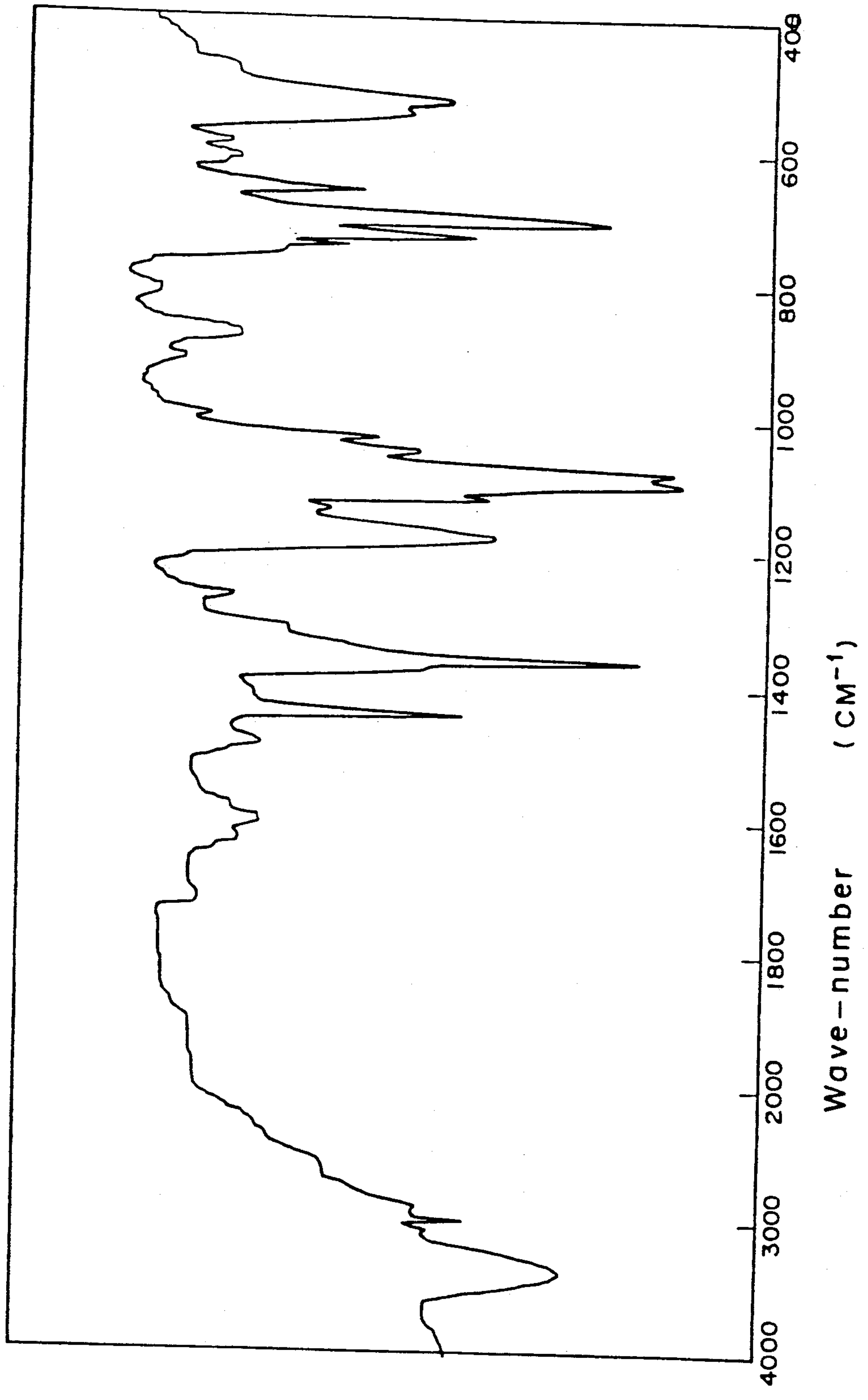
FIG. 17 shows an IR spectrum of the compound of Example 10.
Figure 18:
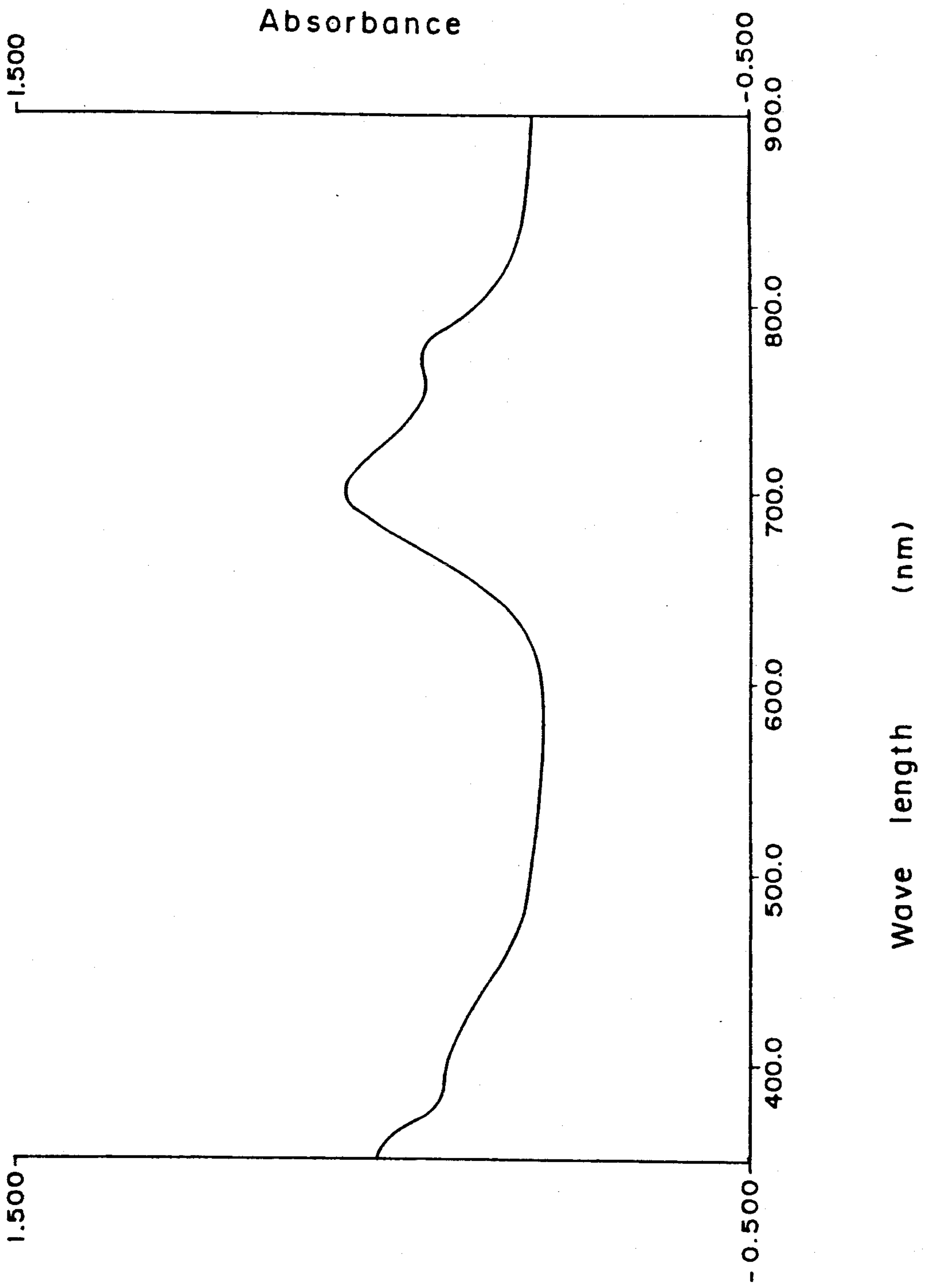
FIG. 18 shows an electron spectrum of the compound of Example 6.

What is claimed is:

1. A naphthalocyanine compound which is represented by the following formula;

[1]

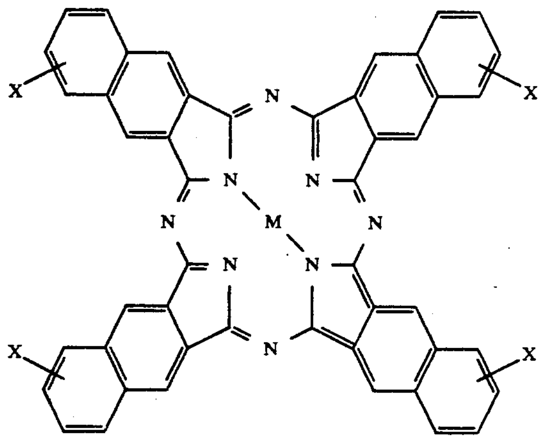

wherein X represents

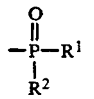

and $R^1$ and $R^2$ respectively represent a hydroxyl group, an alkyl group, an aryl group or an alkoxy group; and M represents 2H, a metal atom, a metal oxide residue or a metal chloride residue.

2. A naphthalocyanine compound as recited in claim 1, wherein $R^1$ and $R^2$ respectively represent hydroxy, ethoxy or phenyl.

3. A naphthalocyanine compound as recited in claim 1, wherein M represents 2H, Cu, Zn, Ni, Co, Fe, Ge, Sn, Pb, Ti, Cr, Mn, Al, In,

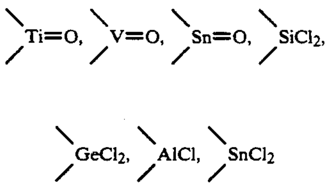

or InCl.

4. A naphthalocyanine compound as recited in claim 1, wherein the substituents X may be substituted at any of the positions 5, 6, 7 or 8 of the naphthalene rings.

5. A naphthalocyanine compound as recited in claim 1, which is tetrakis(diphenylphosphoryl)naphthalocyanine.

6. A naphthalocyanine compound as recited in claim 10, which is tetrakis(diethoxyphosphoryl)naphthalocyanine.

7. A naphthalocyanine compound as recited in claim 1, which is tetrakis(dihydroxyphosphoryl)naphthalocyanine.

8. A naphthalocyanine compound as recited in claim 1, which is tetrakis(diphenylphosphoryl)vanadylnaphthalocyanine.

9. A naphthalocyanine compound as recited in claim 1, which is tetrakis(diphenylphosphoryl)chloroindiumnaphthalocyanine.

* * * * *